United States Patent [19]
Yasui et al.

[11] Patent Number: 5,789,345
[45] Date of Patent: Aug. 4, 1998

[54] GLYPHOSATE LIQUID FORMULATIONS

[75] Inventors: Kenji Yasui, Otsu; Kyuichi Tanaka, Shiga-ken, both of Japan

[73] Assignee: Sankyo Company, Limited, Tokyo, Japan

[21] Appl. No.: 782,515

[22] Filed: Jan. 9, 1997

[30] Foreign Application Priority Data

Jan. 10, 1996 [JP] Japan .................... 2270/1996

[51] Int. Cl.$^6$ .................... A01N 25/22; A01N 57/02
[52] U.S. Cl. .................... 504/206
[58] Field of Search .................... 504/206

[56] References Cited

U.S. PATENT DOCUMENTS

| | | | |
|---|---|---|---|
| 3,977,860 | 8/1976 | Franz | 71/86 |
| 5,302,579 | 4/1994 | Young | 504/206 |
| 5,411,944 | 5/1995 | Young | 504/206 |
| 5,656,572 | 8/1997 | Kuchikata et al. | 504/206 |

FOREIGN PATENT DOCUMENTS

| | | |
|---|---|---|
| 243522 | 11/1987 | European Pat. Off. . |
| 585210 | 3/1994 | European Pat. Off. . |
| 62-111904 | 5/1987 | Japan . |
| 62-242606 | 10/1987 | Japan . |
| 3-56405 | 3/1991 | Japan . |
| 6-157220 | 6/1994 | Japan . |

OTHER PUBLICATIONS

U. Suwunnamek and C. Parker, "Control of Cyperus Rotundus With Glyphosate: The Influence of Ammonium Sulphate and Other Additions", (1975), 13–19, *Weed Research*, 15.

Wyrill et al. "Glyphosate Toxicity to Common Milkweed and Hemp Dogbane by Surfactants," *Weed Science*, 25(3):275–287, May 1977.

*Primary Examiner*—S. Mark Clardy
*Attorney, Agent, or Firm*—Frishauf, Holtz, Goodman, Langer & Chick, P.C.

[57] ABSTRACT

Glyphosate liquid formulations containing surfactants, especially of the amine type, often undergo a yellowish-brown discoloration on storage. This may be inhibited or prevented by incorporating a small amount of urea.

30 Claims, No Drawings

GLYPHOSATE LIQUID FORMULATIONS

BACKGROUND TO THE INVENTION

The present invention relates to a glyphosate liquid formulation which is protected from discoloration, particularly browning, which may occur during storage.

Glyphosate is a known non-selective herbicide. Its chemical name is h-(phosphonomethyl)glycine. It (or one of its salts) is normally employed as a liquid formulation containing a surfactant, often an amine type surfactant.

Although the glyphosate itself is kept stable in such formulations, the liquid formulation tends, on prolonged storage, to develop a yellowish-brown discoloration, which considerably reduces the commercial value of the formulation and may lead to claims from consumers thinking that the discoloration means that the formulation is no longer effective. The reasons for the discoloration are not known and no method of preventing or inhibiting the discoloration has been discovered.

We have now found that the discoloration is a result of the presence of the surfactant in the formulation and that it may be inhibited or altogether prevented by including in the formulation a small amount of urea.

BRIEF SUMMARY OF INVENTION

It is, therefore, an object of the present invention to provide a glyphosate liquid formulation which is protected from discoloration.

Other objects and advantages of the present invention will become apparent as the description proceeds.

The present invention thus provides a stabilized glyphosate liquid formulation containing glyphosate or a salt thereof and a surfactant, wherein there is also present a minor amount of urea in an amount sufficient to inhibit or prevent discoloration.

DETAILED DESCRIPTION OF INVENTION

We have surprisingly found that the yellowish brown discoloration of stabilized glyphosate liquid formulations can be substantially completely prevented from occurring by adding urea.

In the actual manufacture of these liquid formulations, glyphosate is normally neutralized with various types of bases to form a glyphosate salt, which is then employed in the liquid formulation. The bases employed are normally and preferably organic bases, more preferably primary amines, most preferably isopropylamine or trimesyl. In order that the glyphosate should dissolve in water fully and speedily, the base is preferably employed in a slight excess amount rather than in an equimolar amount.

The amount of urea to be added to the glyphosate liquid formulation is small. Suitably, urea is added in an amount of from 0.01 to 1.0 part by weight, preferably in an amount of from 0.05 to 0.5 part by weight, more preferably in an amount of from 0.1 to 0.4 part by weight, based on the weight of the whole liquid formulation.

The mechanism by which the glyphosate liquid formulation is prevented from undergoing yellowish-brown discoloration by adding such small amount of urea has not yet been elucidated. It has been confirmed experimentally that neither glyphosate nor its salts nor the amine surfactants used for stabilization undergo substantial discoloration with time when left to stand by themselves. Accordingly, it is surmised that the discoloration is caused by an interaction between the glyphosate or salt thereof and the surfactant or between impurities contained in the glyphosate or salt thereof and the surfactant. Particularly, when the surfactant is an organic amine, the liquid formulation undergoes notable yellowish-brown discoloration, and the color protecting effect is particularly significant in such cases. In particular, the color protecting effect of the present invention can be demonstrated significantly when the organic amine surfactant is a compound of formula (I):

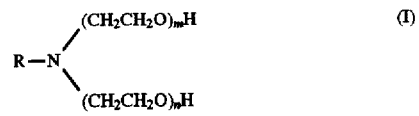

wherein R represents an alkyl group or an alkenyl group; and m and n each are an integer of at least 1, the sum of m and n being from 2 to 40.

The amine surfactant of formula (I) employed in the present invention is preferably derived from natural products. Accordingly, it is not possible to define unambiguously the number of carbon atoms in the alkyl or alkenyl group represented by R. In any particular bulk material, R may be a range or may be expressed as an average, in which case it is unlikely to be a whole number. However, in general, we prefer that the number of carbon atoms in the alkyl or alkenyl group represented by R should be in the range of from 8 to 30, more preferably from 10 to 22 and most preferably from 12 to 20. A particularly preferred example has a range of carbon atoms from 14to 18.

The sum of m and n is preferably from 6 to 30, more preferably from 15 to 25, and most preferably around 20.

There is some prior art in which urea is admixed in a glyphosate liquid formulation. However, they are quite different from the present invention in that the amount of urea to be added is very much greater and that the aim of adding the urea is different from that of the present invention. Therefore, the present invention is clearly distinguished from the known examples. More specifically, while urea-containing glyphosate formulations are disclosed in Japanese Unexamined Patent Publication Nos. Sho 62-242606 and Sho 62-111904, Japanese Unexamined Patent Publication No. Hei 6-157220 and Weed Research, 13, 13, (1975), urea is added so as to enhance the herbicidal effects of glyphosate in these formulations, and the content of urea in each formulation is far greater than that in the present invention. Further, Japanese Unexamined Patent Publication No. Hei 3-56405 also discloses a urea-containing glyphosate formulation, in which urea is added so as to prevent foaming of the liquid formulation, and the content of urea in the formulation is likewise greater than that of the present invention. On the other hand, the small amount of urea added according to the present invention may exhibit a discoloration-preventing effect but it is insufficient to enhance the herbicidal effect or to exhibit the antifoaming effect described in the prior art referred to above.

The glyphosate liquid formulation of the present invention may be prepared by mixing glyphosate, a base (to form a salt), urea, water, an organic amine type surfactant and, if necessary, other additives in any order to dissolve fully the solid contents.

The invention is further illustrated by the following non-limiting Examples. All parts and percentages are by weight.

EXAMPLES (1) Preparation of 2Glyphosate Liquid Formulation 41.86 parts of glyphosate having a purity of 95.57% were added to 42.40 parts of water. When 13.99 parts of isopropylamine were added to the mixture, with stirring, the glyphosate started to dissolve in the water with heat generation. A further 1.75 parts of isopropylamine were then added to the mixture and stirring was continued. As a result, the glyphosate dissolved completely to give a glyphosate-isopropylamine solution containing 40.01 parts of glyphosate.

Subsequently, eleven samples of a urea-containing liquid formulation were prepared by mixing 78.96 parts of this solution, 13.0 parts of NEWCOL TA-420 [an amine type surfactant, prepared by adding 20 mol of ethylene oxide to beef tallow amine: a compound having the formula (I), wherein R represents an alkyl group having from 14 to 18 carbon atoms; and the sum of m and n is 20], and urea in an amount of 0.05 part, 0.10 part, 0.15 part, 0.20 part, 0.25 part, 0.30 part, 0.35 part, 0.40 part, 0.50 part, 0.75 part or 1.0 part, the balance being water. As a control, a liquid formulation containing no urea was also prepared.

(2) Heat Aging Test

The resulting glyphosate liquid formulations containing urea and the control glyphosate liquid formulation containing no urea were each pipetted in an amount of 25 ml into 30 ml colorless glass vials (X) or into 30 ml brown glass vials (Y), and the brown glass vials were each covered on the outer surface with aluminum foil so as to intercept light. These samples were stored at 40° C. for 30 days (Group A), for 60 days (Group B) or for 90 days (Group C), or at 50° C. for four weeks (Group D), for 8 weeks (Group E) or for 12 weeks (Group F).

(3) Assay of Discoloration Degree

The degrees of discoloration of each sample measured before and after the heat aging test are expressed by the Gardner color scale number according to the General Test Method for Coatings; JIS K5400 4.3. However, this test method expresses the degree of discoloration by the gradation in the yellowness. The yellowish-brown discoloration of the glyphosate liquid formulations over a period cannot therefore be expressed exactly. Accordingly, in addition to the evaluation by the Gardner color scale number, those samples which underwent browning are marked with "**" and those which underwent light browning are marked with "*" so as to express the degree of discoloration more exactly. The results are shown in the following Table 1.

color scale number, which indicates the yellow-color gradation, and also discoloring, i.e. browning, which is assessed visually.

We claim:

1. A stabilized glyphosate liquid formulation comprising glyphosate or a salt thereof and a surfactant, wherein urea is also present a minor amount sufficient to inhibit or prevent discoloration of the stabilized glyphosate liquid formulation and the amount of the urea being insufficient to enhance the herbicidal effect of the glyphosate and insufficient to exhibit an antifoaming effect.

2. A glyphosate liquid formulation according to claim 1, wherein the content of urea is from 0.01 to 1.0 part by weight per 100 parts by weight of the liquid formulation.

3. A glyphosate liquid formulation according to claim 2, wherein said glyphosate is in the form of its isopropylamine salt.

4. A glyphosate liquid formulation according to claim 2, wherein the content of urea is from 0.05 to 05 part by weight per 100 parts by weight of the liquid formulation.

5. A glyphosate liquid formulation according to claim 4, wherein said glyphosate is in the form of its isopropylamine salt.

6. A glyphosate liquid formulation according to claim 4, wherein the content of urea is from 0.1 to 0.4 part by weight per 100 parts by weight of the liquid formulation.

7. A glyphosate liquid formulation according to claim 6, wherein said glyphosate is in the form of its isopropylamine salt.

8. A glyphosate liquid formulation according to any of claims 1 or 4, wherein said surfactant is an organic amine.

9. A glyphosate liquid formulation according to claim 8, wherein said glyphosate is in the form of its isopropylamine salt.

10. A glyphosate liquid formulation according to claim 8, wherein said organic amine is a compound of formula:

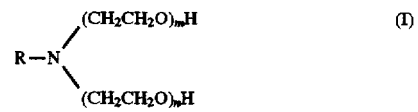

wherein R represents an alkyl group or an alkenyl group; and m and n are each an integer of at least 1, the sum of m and n being from 2 to 40.

TABLE 1

| Urea content Before heat aging | 0 | 0.05 | 0.1 | 0.15 | 0.2 | 0.25 | 0.3 | 0.35 | 0.4 | 0.5 | 0.75 | 1.0 |
|---|---|---|---|---|---|---|---|---|---|---|---|---|
| After heat aging | 5 | 6 | 6 | 6 | 6 | 6 | 6 | 6 | 6 | 6 | 6 | 6 |
| Group XA | 7** | 6** | 6 | 6 | 5 | 5 | 5 | 5 | 4–5 | 4 | 4–5 | 4–5 |
| Group XB | 7** | 6** | 6 | 6 | 5 | 5 | 5 | 5 | 5 | 4 | 5 | 5 |
| Group XC | 8** | 7** | 6 | 5 | 5 | 5 | 5 | 4 | 4 | 4 | 4 | 4 |
| Group XD | 7** | 7** | 6 | 6 | 5 | 5 | 5 | 4 | 4 | 4 | 5 | 5 |
| Group XE | 8** | 7** | 6 | 6 | 6 | 6 | 6 | 5 | 5 | 5 | 5 | 5 |
| Group XF | 8** | 7** | 6* | 6* | 6* | 6 | 6 | 5 | 5 | 5 | 5 | 5 |
| Group YA | 7** | 6** | 6–7 | 6 | 5 | 5 | 5 | 5 | 5 | 4 | 5 | 5 |
| Group YB | 7** | 6** | 6 | 6 | 6 | 5 | 5 | 5 | 5 | 5 | 5 | 5 |
| Group YC | 8** | 7** | 6 | 6 | 5 | 5 | 5 | 5 | 4 | 4 | 4 | 4 |
| Group YE | 10** | 8** | 7** | 6 | 6 | 6 | 6 | 5 | 5 | 5 | 5 | 5 |
| Group YF | 8** | 7** | 7** | 7** | 7 | 6 | 6 | 6 | 6 | 6 | 5 | 5 |

As is clearly demonstrated by the above Examples, discoloration of glyphosate liquid formulations can be noticeably prevented by adding urea thereto. It is a specific effect of the present invention to prevent significantly the yellowing of such liquid formulations as expressed by the Gardner 11. A glyphosate liquid formulation according to claim 10, wherein said glyphosate is in the form of its isopropylamine salt.

12. A glyphosate liquid formulation according to claim 10, wherein R represents an alkyl or alkenyl group having from 8 to 30 carbon atoms.

13. A glyphosate liquid formulation according to claim 12, wherein said glyphosate is in the form of its isopropylamine salt.

14. A glyphosate liquid formulation according to claim 12, wherein the sum of m and n is from 6 to 30.

15. A glyphosate liquid formulation according to claim 14, wherein said glyphosate is in the form of its isopropylamine salt.

16. A glyphosate liquid formulation according to claim 10, wherein R represents an alkyl or alkenyl group having from 14 to 18 carbon atoms.

17. A glyphosate liquid formulation according to claim 16, wherein said glyphosate is in the form of its isopropylamine salt.

18. A glyphosate liquid formulation according to claim 16, wherein the sum is about 20.

19. A glyphosate liquid formulation according to claim 18, wherein said glyphosate is in the form of its isopropylamine salt.

20. A glyphosate liquid formulation according to claim 10, wherein the sum of m and n is from 6 to 30.

21. A glyphosate liquid formulation according to claim 20, wherein said glyphosate is in the form of its isopropylamine salt.

22. A glyphosate liquid formulation according to claim 10, wherein the sum is about 20.

23. A glyphosate liquid formulation according to claim 22, wherein said glyphosate is in the form of its isopropylamine salt.

24. A glyphosate liquid formulation according to claim 1, wherein said glyphosate is in the form of its isopropylamine salt.

25. A glyphosate liquid formulation according to claim 1, wherein the urea is in an amount of 0.3 to 0.75 part by weight per 100 parts by weight of the liquid formulation.

26. A glyphosate liquid formulation according to claim 1, wherein the urea is in an amount of 0.3 to 1.0 part by weight per 100 parts by weight of the liquid formulation.

27. A glyphosate liquid formulation according to claim 1, wherein the urea is in an amount of 0.5 to 0.75 part by weight per 100 parts by weight of the liquid formulation.

28. A glyphosate liquid formulation according to claim 1, wherein the urea is in an amount of 0.5 to 1.0 part by weight per 100 parts by weight of the liquid formulation.

29. A glyphosate liquid formulation according to claim 1, wherein the surfactant is an organic amine prepared by adding ethylene oxide to a beef tallow amine, said organic amine being of the formula

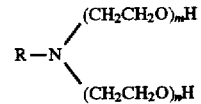

wherein R is an alkyl group having 14 to 18 carbon atoms; m and n each are an integer of at least 1 and the sum of m and n is 20.

30. A glyphosate liquid formulation according to claim 29, wherein the urea is in an amount of 0.5 to 0.75 part by weight per 100 parts by weight of the liquid formulation and said glyphosate is in the form of its isopropylamine salt.

* * * * *

UNITED STATES PATENT AND TRADEMARK OFFICE
CERTIFICATE OF CORRECTION

PATENT NO. : 5,789,345
DATED : August 4, 1998
INVENTOR(S) : YASUI et al

It is certified that error appears in the above-identified patent and that said Letters Patent is hereby corrected as shown below:

Column 2, line 65: after "of", delete "2".

Column 4, line 29 (Claim 8): replace "1 or 4" with --1, 3, 4 or 5--.

Signed and Sealed this

Thirty-first Day of August, 1999

Attest:

Q. TODD DICKINSON

Attesting Officer

Acting Commissioner of Patents and Trademarks